(12) United States Patent
Poteet et al.

(10) Patent No.: US 8,368,034 B2
(45) Date of Patent: Feb. 5, 2013

(54) SUBSTANCE DETECTION, INSPECTION AND CLASSIFICATION SYSTEM USING ENHANCED PHOTOEMISSION SPECTROSCOPY

(75) Inventors: Wade Poteet, Vail, AZ (US); James Ryles, Tucson, AZ (US); Malcolm Philips, Cornelius, NC (US)

(73) Assignee: Cdex, Inc., Tucson, AZ (US)

( * ) Notice: Subject to any disclaimer, the term of this patent is extended or adjusted under 35 U.S.C. 154(b) by 0 days.

(21) Appl. No.: 13/064,626

(22) Filed: Apr. 4, 2011

(65) Prior Publication Data

US 2012/0056093 A1 Mar. 8, 2012

Related U.S. Application Data (63) Continuation-in-part of application No. 11/822,020, filed on Jun. 29, 2007, now abandoned.

(60) Provisional application No. 60/817,101, filed on Jun. 29, 2006.

(51) Int. Cl.
*G01N 21/64* (2006.01)

(52) U.S. Cl. .................................. 250/461.1
(58) Field of Classification Search ............... 250/461.1
See application file for complete search history.

(56) References Cited

U.S. PATENT DOCUMENTS

| | | | | | |
|---|---|---|---|---|---|
| 3,829,696 | A | * | 8/1974 | Birnbaum | 250/365 |
| 4,469,946 | A | * | 9/1984 | Tanaka et al. | 250/373 |
| 2003/0164456 | A1 | * | 9/2003 | Petrich et al. | 250/458.1 |
| 2005/0077476 | A1 | * | 4/2005 | Poteet et al. | 250/461.1 |
| 2005/0229698 | A1 | * | 10/2005 | Beecroft et al. | 73/300 |
| 2006/0279732 | A1 | * | 12/2006 | Wang et al. | 356/326 |
| 2007/0098391 | A1 | * | 5/2007 | Howard et al. | 396/155 |

* cited by examiner

*Primary Examiner* — Kiho Kim
(74) *Attorney, Agent, or Firm* — Millen, White, Zelano & Branigan, P.C.; William F. Nixon (57) ABSTRACT

A handheld or portable detection system with a high degree of specificity and accuracy, capable of use at small and substantial standoff distances (e.g., greater than 12 inches) is utilized to identify specific substances and mixtures thereof in order to provide information to officials for identification purposes and assists in determinations related to the legality, hazardous nature and/or disposition decision of such substance(s). The system uses a synchronous detector and visible light filter to enhance detection capabilities.

15 Claims, 5 Drawing Sheets

SUBSTANCE DETECTION, INSPECTION AND CLASSIFICATION SYSTEM USING ENHANCED PHOTOEMISSION SPECTROSCOPY

CROSS-REFERENCE TO RELATED APPLICATIONS

This application is a Continuation-In-Part of U.S. patent application Ser. No. 11/822,020, filed on Jun. 29, 2007, which claims the benefit of U.S. Provisional Patent Application No. 60/817,101, filed on Jun. 29, 2006, both of which are hereby incorporated by reference.

FIELD OF THE INVENTION

The invention relates generally to the field of substance and material detection, inspection, and classification at wavelengths between approximately 200 nm and approximately 1800 nm. In particular, a handheld Enhanced Photoemission Spectroscopy ("EPS") detection system with a high degree of specificity and accuracy is utilized to identify specific substances and mixtures thereof in order to provide information to officials for identification purposes and assists in determinations related to the legality, hazardous nature or disposition decision of such substance(s).

DISCUSSION OF THE RELATED ART

Ultraviolet to Near Infrared ("UV to NIR") EPS is an analytical technique used to identify and characterize chemical and biological materials and compositions. Modern light sources and detectors have made true handheld operation (as opposed to "transportable") possible, and unique signal processing techniques increase sensitivity of these systems to allow detection of trace amounts of materials on surfaces. In operation, UV to NIR EPS systems direct energy (in the form of concentrated photons) from an excitation source toward a target area using, for example, reflective or refractive optics. Photoelectric and other interactions of the photons with the sample material produce detectable wavelength-shifted emissions that are typically at longer wavelengths than the absorbed excitation UV to NIR photons, and specular reflection or absorption produces selected wavelength-specific portions of the originating energy.

The first process involves a wavelength shift that is due to an energy transfer from the incident photons (at a specific wavelength) to the target materials. The transferred energy causes some of the sample's electrons to either break free or enter an excited (i.e., higher) energy state. Thus, these excited electrons occupy unique energy environments that differ for each particular molecular species being examined.

As a result, electrons from higher energy orbital states "drop down" and fill orbitals vacated by the excited electrons. The energy lost by the electrons going from higher energy states to lower energy states results in an emission spectrum unique to each substance. When this process occurs in a short time, usually 100 nanoseconds or less, the resultant photon flux emission is referred to as fluorescence, although luminescence, phosphorescence, and photoluminescence are frequently used to describe these processes as well.

The second process involves scattering of the incident energy by the target material due to its vibrational state; this process is known as Raman scattering, and occurs in a relatively narrow band of wavelengths that result from the incident energy being in the correct range to excite the phenomenon. The third component of EPS involves specular reflection or absorption from the surface of the target material so that only selective portions of the incident energy spectrum are reflected, while others are absorbed.

The resultant emission spectrum generated is detected with a spectrograph, digitized and analyzed (i.e., wavelength discrimination) using unique algorithms and signal processing. Each different substance within the target area produces a distinctive spectrum that can be sorted and stored for comparison during subsequent analyses of known or unknown materials.

UV to NIR EPS does have some drawbacks. First, it can be affected by interference (or clutter). Interference is defined as unwanted UV to NIR flux reaching the detector that does not contribute directly to the identification of a material of interest. For example, when attempting to detect illegal substance on clothing, clutter can arise from exciting unimportant molecules in the target area, exciting materials close to the detector/emitter region, external flux from outside the target area (including external light sources like room lights or the sun) and scattering from air and/or dust in the light path.

UV to NIR EPS systems also are limited in terms of sensitivity distances. Greater distances between the substance of interest and the UV to NIR excitation source and detector result in weaker return photon flux (i.e., weaker, if any, EPS) from the sample material.

Conventional spectroscopy and detection techniques include, among other things, neutron activation analysis, ultraviolet absorption, ion mobility spectroscopy, scattering analysis, nuclear resonance, quadrupole resonance, near infrared (NIR) reflectance spectroscopy, selectively-absorbing fluorescent polymers, and various chemical sensors. Each of these methodologies, however, suffers from deficiencies.

For example, neutron activation analyses, while capable of directly measuring ratios of atomic constituents (e.g., hydrogen, oxygen, nitrogen, and carbon) require bulky energy sources that have high power demands and thus do not lend themselves to handheld instruments. Traditional UV to NIR absorption and scattering techniques are subject to high degrees of inaccuracy (i.e., false alarms and omissions) absent sizeable reference resources and effective predictive analysis systems. Scattering analysis techniques suffer similar shortcomings.

Ion mobility spectroscopy devices are currently in use at many airports for "wiping" analysis, but suffer from low sensitivities in practical measuring scenarios and have high maintenance demands. Resonance Raman is an emerging and promising technology, but requires special surfaces and sample preparation for operation. Quadrupole resonance techniques offer a good balance of portability and accuracy, but are only effective for a limited number of materials (i.e., they have an extremely small range of materials they can reliably and accurately detect). These systems also suffer from outside interfering radio frequency sources such as terrestrial radio broadcast stations.

Finally, chemical sensors such as conventional NIR devices, while very accurate, are slow acting, have extremely limited ranges, and are too bulky for convenient handheld operation. Furthermore, chemical vapor sensors do not always produce consistent results under varying environmental conditions (e.g., high humidity and modest air currents) when substantial standoff distances are involved.

SUMMARY OF THE INVENTION

The invention relates generally to the field of substance and material detection, inspection, and classification at wavelengths between approximately 200 nm and approximately 1800 nm. In particular, a handheld Enhanced Photoemission Spectroscopy ("EPS") detection system with a high degree of specificity and accuracy, capable of use at small and substantial standoff distances (e.g., greater than 12 inches) is utilized to identify specific controlled substances and their mixtures in order to provide information to officials so that determinations can be made as to the legality and/or hazardous nature of such substance(s).

Thus, the invention relates to a handheld system, process, and method for material detection, inspection, and classification. In particular, the invention includes a miniature electronic scanning detection system (e.g., an EPS spectrograph) with a high degree of specificity and accuracy, operating generally in the ultraviolet to near infrared portion of the electromagnetic spectrum that is used to identify specific individual and unique mixtures of substances (including remote, real-time measurements of individual chemical species in complex mixtures).

The unique spectral emissions from common controlled substances allow the process to be applied to materials such as narcotics, illicit drugs, explosives, and toxic chemicals have also been observed with models of this instrument. The substances may additionally include food types, synthetic drugs, prescribed narcotics, liquids, powders and the like.

The invention provides a highly specific detection approach that directly addresses two major classes of technical challenges: (1) standoff detection of low levels of substance deposition on or under a variety of surfaces in highly variable circumstances with (2) an extremely low false alarm rate.

Miniaturizing an EPS detection system to a handheld unit sizes involves significant technological and engineering improvements over presently available spectrometer systems and light sources. For example, recently developed and commercially available light emitting diodes (LED's) can provide the necessary illumination and a bandpass filter of the proper wavelength can be utilized in front of the LED, so that only the molecules of interest are excited (the physical beam pattern of these LED's is such that two LED's, rotated so that their beam patterns are orthogonal to other, may be used for uniform illumination of the target of interest).

Additionally, the miniaturization of spectrometer components usually reduces overall sensitivity, so in order to increase the system sensitivity to the required level for trace detection of materials, a low-pass spectral filter (such as that illustrated herein) can be introduced into the receiving optical path prior to the spectrometer. This introduction of a low-pass spectral filter reduces unwanted light from the external environment, e.g., sunlight reduction for the UV implementation of this invention, as well as narrows the spectral bandwidth to improve the signal to noise ratio. Increases in signal to noise ratio can also be realized from suitable digital filtering techniques.

Further, modulating the light source(s) and utilizing phase sensitive (synchronous) detection along with advanced algorithms further improves the signal to noise ratio, which is directly related to the limit of minimum detection as well as the false positive rate. Improved signal to noise ratios, along with additional signal processing (algorithms include, but are not limited to, correlation, matched filters, mean squared error, and likelihood ratio comparisons) enhances detection as well.

The invention includes a handheld EPS detections system including (a) a miniature scanning detection system operating in the ultraviolet to near infrared portion of the electromagnetic spectrum that includes (i) an excitation light source; (ii) a bandpass filter; (iii) a low-pass spectral filter; and (iv) an ultraviolet fluorescence detector; (b) a processor coupled to the ultraviolet fluorescence detector, the processor receiving spectral data from the ultraviolet fluorescence detector; and (c) a database coupled to said processor that includes signature data for a plurality of predetermined chemical substances.

In another aspect, the invention includes an EPS detection system that can include a concentrator including a vacuum device (e.g., portable vacuum cleaner) operatively coupled to the EPS detections system with filter material over the intake to draw particles from the environment surrounding the area of interest and where a filter is then used as the target. This arrangement facilitates detection of airborne particles of the material of interest.

In another aspect, the EPS detection system of the invention emits light from single or multiple light sources, such as from an LED, laser, laser diode or flashlamp, to excite emission in different substances as well as exciting different emissions in the same substance. The light source may be pulsed, square-wave modulated, and/or continuous wave and may include single and/or multiple sources for complete scene illumination (e.g., rotate LED's, etc.).

In another aspect, the EPS detection system of the invention gathers spectral signatures with a spectrally selective detector, including conventional spectrometers, spectrally filtered photodetectors, spectrometers using Multimodal Multiplex Spectroscopy™, or any other form of spectral detection. In another aspect, the EPS detection system of the invention digitizes the obtained spectral signatures.

In another aspect, the EPS detection system applies unique algorithms for signal processing, including, but not limited to, embedded processors using filtered FFT, synchronous detection, phase-sensitive detection, digital filters unique to each particular substance being detected. It is important to note that one, two, or all three physical processes (photoemission, Raman scattering, or specular reflection or absorption) may be present in a particular detection scenario. When only total return energy in a specific band of wavelengths is being utilized to detect the target material, then all three processes produce the total measured spectral energy in the wavelength band and the total return signal amplitude in a range of wavelengths can produce the desired signal for analysis and display.

When more specificity is required, a frequency-space data transformation following digitization (e.g., FFT) allows the influence of each of the three processes to be separated by examining the individual coefficients of the transform series. Because certain coefficients are affected more by one process than another in this type of transform, deconvolution of the process creating the overall spectrum is possible.

In another aspect, the EPS detection system of the invention uses algorithms to compare the obtained spectral signatures to a database of known and/or previously obtained spectral signatures. These algorithms can include, but are not limited to, correlation, matched filters, mean squared error, Laplace transforms, Fourier transforms, least-squares, or likelihood ratio tests.

In another aspect, the EPS detection system of the invention displays the obtained spectral signatures and/or the results of a comparison of the obtained spectral with signatures to a database of known and/or previously obtained spectral signatures. In another aspect, the EPS detection system of the invention includes a handheld and/or battery operated device EPS detection device. In another aspect, the EPS detection system of the invention includes a GPS locater internally mounted within the EPS detection system and/or in a handheld component of such system.

In another aspect, the EPS detection system of the invention determines the distance to target in order to keep the system within a sensitive range and could adjust the detection threshold as a function of distance. In another aspect, the EPS detection system of the invention communicates wirelessly to a remote location. In another aspect, the EPS detection system of the invention includes cell phone and/or other remote access communications capabilities, including video functions and storage.

BRIEF DESCRIPTION OF THE DRAWINGS

The accompanying drawings are included to provide further understanding of the invention and constitute a part of the specification. The drawings listed below illustrate embodiments of the invention and, together with the description, serve to explain the principles of the invention, as disclosed by the claims and their equivalents.

DETAILED DESCRIPTION OF THE PREFERRED EMBODIMENTS

Aspects of the invention are disclosed in the accompanying description. Alternate embodiments of the present invention and their equivalents are devised without parting from the spirit or scope of the present invention. It should be noted that like elements disclosed below are indicated by like reference numbers in the drawings.

The invention relates to a system and methods for material detection, inspection, and classification. In particular, an electronic scanning detection system (e.g., an EPS spectrograph) with a high degree of specificity and accuracy, operating in the ultraviolet to near infrared portion of the electromagnetic spectrum, is used to identify specific individual and unique mixtures of substances (including remote, real-time measurements of individual chemical species in complex mixtures).

Preferably, the substances identified by the invention are exposed medications and/or explosive and/or illegal materials that are not otherwise labeled or hidden within a sealed, opaque container. Certain embodiments of the invention, however, may be able to detect substances in a cup, bottle, or other container. This feature may be desirable for quality assurance programs to evaluate and monitor substances before leaving a manufacturing facility or pharmacy prior to delivery.

The invention may be configured in any number of ways, including as a hand-held device, a mobile device and/or fixed mounted device. In one embodiment, the invention is capable of electronically scanning substances directly or of receiving data from an accessible scanning device. In one embodiment, identification of a substance includes analysis of the substance's electromagnetic spectrum. A generated spectrum can be cross-correlated and analyzed by comparison against other known reference information (e.g., other drugs or substances being administered to a patient in view of known genetic or health factors, known drug interactions and/or quality assurance information). The disclosed embodiments are usable without changing the physical appearance or chemical composition of the substances.

The invention has an extensive number of applications. A non-exclusive list includes, but is not limited to: any industries, processes and/or equipment requiring remote, non-invasive sensing of multiple chemical compounds or constituents (such as monitoring, commercial drug quality control and/or medication dispensing verification). Reliable detection of trace amounts of controlled substances is required in a variety of settings because the raw ingredients to manufacture these substances are widely available, and currently no detection exists that is rapid, non-contact, and handheld.

Figure 1A:
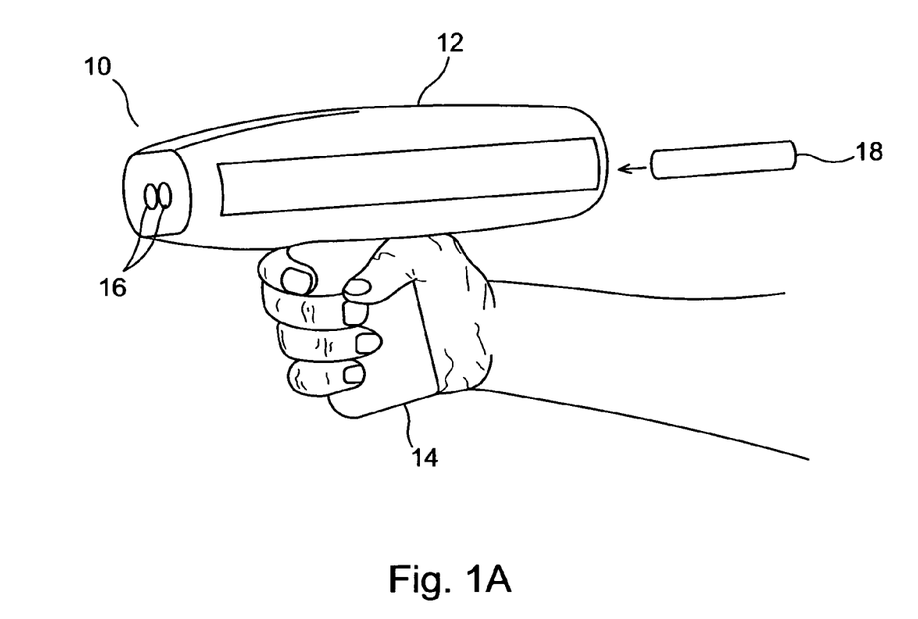
FIG. 1A illustrates a detection system used as a hand-held device according to the disclosed embodiments.
Figure 1B:
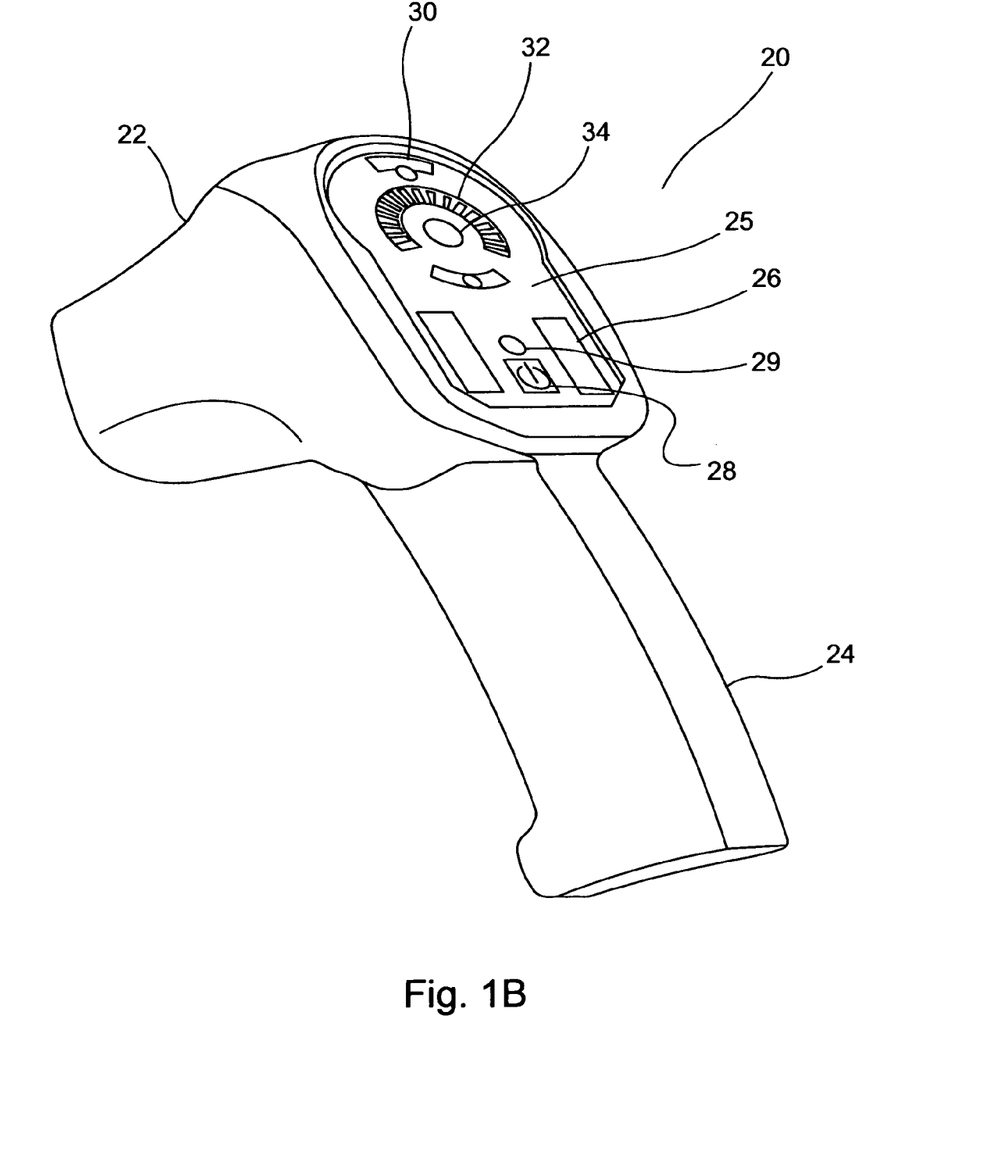
FIG. 1B illustrates another detection system also used as a hand-held device according to the disclosed embodiments.
Figure 1C:
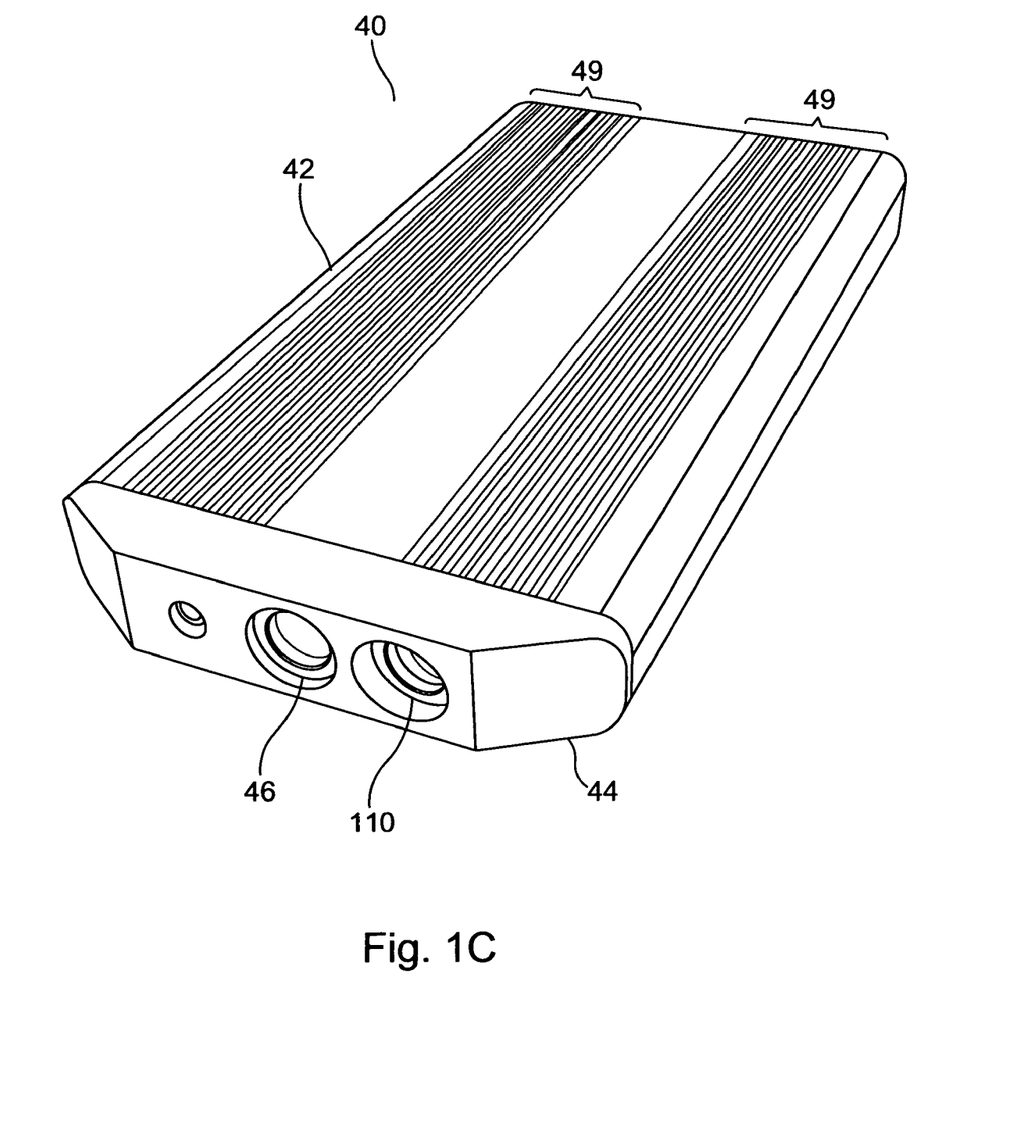
FIG. 1C illustrates another detection system also used as a portable device according to the disclosed embodiments.

The detection systems shown in FIGS. 1A-C may include a miniature flash lamp with spectral filtering to provide the appropriate excitation energy to induce (simultaneously) photoemission, Raman scattering, and NIR absorption/reflection in the target.

In order to improve the standoff distance and the size of the footprint of the detector, a source with more effective power in the required excitation spectral band will be used. Candidates include lasers, laser diodes, light emitting diodes, and more powerful flash lamps. Commercial light emitting diodes (LEDs) are beginning to be available that can provide energy on the target that is approximately 100 times greater than conventional energy sources. As such, the same detection threshold that is used in the present detector can be maintained while increasing the standoff distance from approximately 2 inches to approximately 12 inches and the effective detection footprint can be increased from approximately 1 inch to approximately 2¾ inches.

In the disclosed system, detection of the return photoemission is currently accomplished using a miniature custom spectrometer. While this approach allows straightforward re-configuration to detection of emission from additional substances at other wavelengths, several other schemes can provide sufficient spectral detection include individual photodiode detector/spectral filter combinations as well as lower cost and smaller size spectrometer designs. The resolution of the current spectrometer is greater than is required for this application, so the spectrometer approach may prove viable in a lower-resolution version.

The invention can include any known scanning device or combinations thereof. Computer and control electronics can also be connected to or used in tandem with the invention. The invention includes a handheld EPS detections system including (a) a miniature scanning detection system operating in the ultraviolet to near infrared portion of the electromagnetic spectrum that includes (i) an excitation light source; (ii) a bandpass filter; (iii) a low-pass spectral filter; and (iv) an ultraviolet fluorescence detector; (b) a processor coupled to the ultraviolet fluorescence detector, the processor receiving spectral data from the ultraviolet fluorescence detector; and (c) a database coupled to said processor that includes signature data for a plurality of predetermined chemical substances.

The disclosed systems may include an optical scanning device, a spectrograph (if this technique is used), a detector and an energy source. The disclosed system also may include a scanning device that is portable and/or that has no input keyboard or monitor screen. In this embodiment, the scanning detection device communicates using an input spectrograph and an output of a series of lights (e.g., green, yellow, blue, red and the like) mounted on the scanning device.

The disclosed system also may include an EPS detection system that can include a concentrator for airborne materials comprising a vacuum device (e.g., portable vacuum cleaner)

operatively coupled to the EPS detections system with filter material over the intake to draw particles from the environment surrounding the area of interest and where a filter is then used as the target. The EPS detection system of the invention emits light from single or multiple light sources, such as from an LED, laser, laser diode or flashlamp, to excite emission in different substances as well as exciting different emissions in the same substance. The light source may be pulsed, square-wave modulated, and/or continuous wave and may include single and/or multiple sources for complete scene illumination (e.g., rotate LED's, etc.).

The EPS detection system of the invention may gather spectral signatures with a spectrally selective detector, including, for example, conventional spectrometers, spectrally filtered photodetectors, spectrometers using Multimodal Multiplex Spectroscopy™, or any other form of spectral detection. In another aspect, the EPS detection system digitizes the obtained spectral signatures. The EPS detection system applies unique algorithms for signal processing, including, but not limited to embedded processors using filtered FFT, synchronous detection, phase-sensitive detection, digital filters unique to each particular substance being detected.

The EPS detection system compares the obtained spectral signatures to a database of known and/or previously obtained spectral signatures. In another aspect, the EPS detection system of the invention displays the obtained spectral signatures or the results of a comparison of the obtained spectral with signatures to a database of known or previously obtained spectral signatures.

The EPS detection system may include a handheld or battery operated device EPS detection device. The EPS detection system also may include a GPS locater internally mounted within the EPS detection system or in a handheld component of such system. The EPS detection system determines the distance to target in order to keep the system within a sensitive range. The EPS detection system also may communicate wirelessly to a remote location. The EPS detection system may include cellular or other remote access communications capabilities.

In general, the disclosed system provides a mechanism for collecting unique "fingerprint" identifications (i.e., gathers information such that the fingerprint may be determined in a timely manner) of target materials that are used to distinguish them from other similar substances without prior knowledge of the substance (i.e., no single "unique identifiers" required). The fingerprint may include any quantifiable characteristic(s) pertaining to the substance, such as excitation wavelengths, barcodes, electronic signatures, and the like, negating any requirement for a single unique identifier. The disclosed system also may include an accessible database of known characteristic(s) pertaining to certain agents and substances. An accessible computer system or other storage means enables the time, place and type of substance administered to be documented.

A broadband source may be used to generate EPS within a target area causing detectable emission at UV to NIR wavelengths that can be uniquely matched to known materials.

In another embodiment of the invention, the system can be used to simultaneously evaluate a group of different substances' for example, methamphetamine and TATP explosive. In this embodiment, the operator can be permitted to manipulate a combined spectrum of a group of different powders, or other chemical substances, and use the combined spectra to identify unauthorized or inappropriate variations. Such variations can include dangerous mixtures of partially completed mixes or additions and/or quality control verifications. Spectra of individual substances can also be combined to identify specific substances such as pharmaceuticals and explosives.

The detection of emission photons is accomplished with a receiver that includes optics, a spectrograph, and a detector array. The disclosed system may include an analysis system that identifies particular substances of interest. The disclosed system preferably operates within the UV to NIR radiation wavelength range of approximately 200 nanometers to approximately 1800 nanometers. The disclosed system, however not limited to this wavelength range as the invention can operate within other wavelength ranges.

Multispectral excitation and/or detection is accomplished with the invention in a number of ways. Selection and control of either excitation wavelengths and/or detection wavelengths can be accomplished using, among other things, a pulsed power sources (e.g. a sequence-pulsed laser system) in conjunction with data collection corresponding to each pulse, a spectral filter wheel(s) to select or vary different excitation or detection wavelengths and combinations thereof. The commercial availability of LED's allows miniaturization and power consumption optimization of the handheld system.

The features disclosed above may be incorporated within a detection system. Examples of hand-held or stand-alone detection systems are shown in FIGS. 1A-C. FIG. 1A depicts a detection system 10 used as a hand-held device according to the disclosed embodiments. Detection system 10 includes housing 12 which includes the electronics and components to perform the detection functions. These elements are disclosed in greater detail below.

Detection system 10 also includes hand grip 14 below housing 12. Hand grip 14 may house the power supply or batteries for detections system 10. The front of housing 12 includes through-holes 16 that allow light or energy to be directed and captured when detection system 10 is in operation. Detection system 10 may include additional through-holes as needed.

Housing 12 of detection system 10 also may include a compartment to receive cartridge 18. Cartridge 18 may store data for detecting specified substances so that detection system 10 does not require a wireless or remote connection. This feature may be desired in those areas where wireless networks do not exist, yet the need for a portable system exists. Cartridge 18 may house a hard-drive or other means for storing the database for spectral signatures. Cartridge 18 also may store instructions to operate detection system 10. Cartridge 18 also may be placed in the top of detection system 10, or within hand grip 14.

FIG. 1B depicts a detection system 20 also used as a handheld device according to the disclosed embodiments. Detection system 20 includes a housing 22 and hand grip 24, much like detection system 10. Housing 22, however, differs from housing 12 in that it slopes downward away from the user, and is smaller to fit within cramped areas. Detection system 20 may be used in buildings or in security operations involving compartments such as airplanes, trains, ships or automobiles. The user may place detection system 20 within the compartment to detect substances on the floor or bottom of the compartment.

Detection system 20 also includes back panel 25 that provides visual indication to the user of the results of detection operations. Scan button 26 may initiate detection operations. Power button 28 toggles detection system 20 on and off, with an "on" state being shown by power indicator 29. Indicator 30 may show that detection system 20 is operating and in the process of receiving signals back from the target substance. Bar indicator 32 may show the intensity level of the received signals back to detection system 20. If the levels are not high enough, then detection operations may be re-initiated. Indicator 34 shows that the target substance matches the spectral data of a substance of interest, such as explosives or drugs.

FIG. 1C depicts a detection system 40 used as a portable device according to the disclosed embodiments. Detection system 40 includes housing 42 and front part 44. Detection system 40 does not include a hand grip, and is similar in size to a personal digital assistant. Ridges 49 help distinguish detection system 40 from other devices that the user may handle.

Front part 44 includes an aperture for allowing a light source 110 to send a beam of light towards a target. The light is reflected off the target, and received at detector screen 46. The internal components of detection system are disclosed in greater detail below. Front part 44 may be removable from housing 42 so that different filters may be used to detect different materials.

Figure 2:
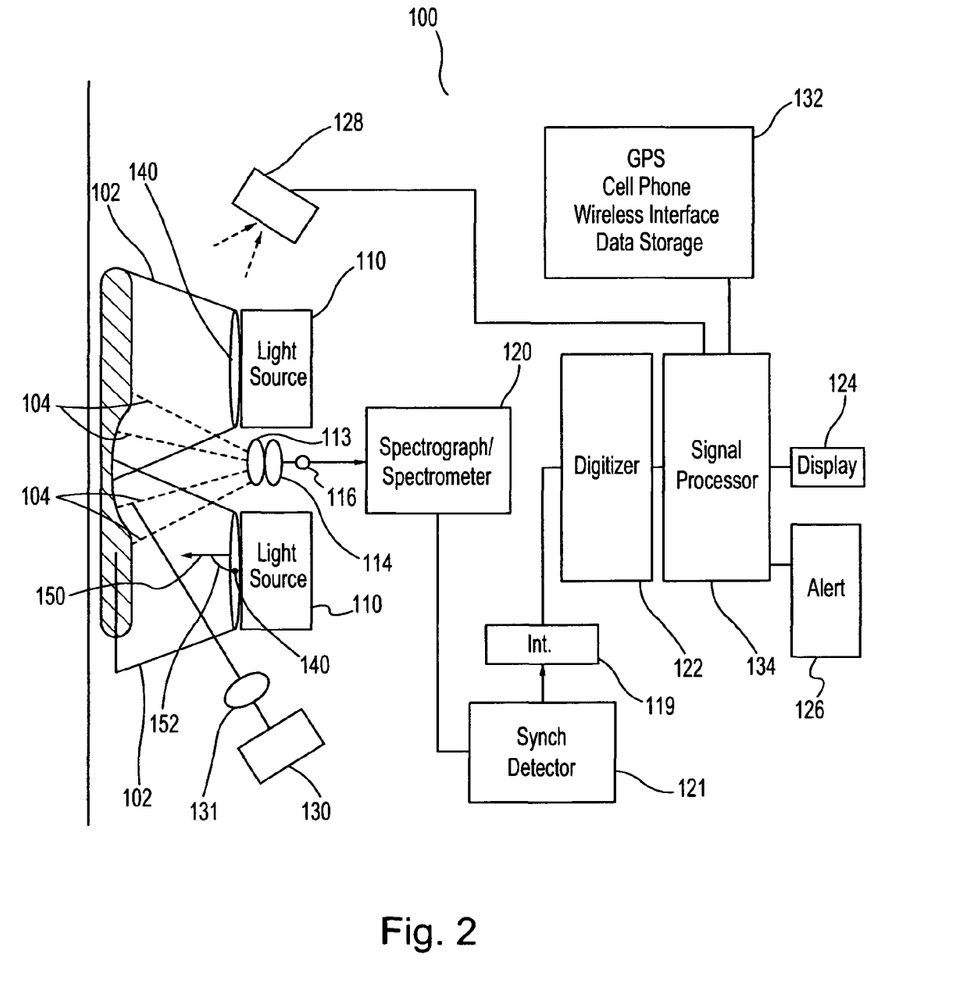
FIG. 2 illustrates a low-pass spectral filter detection system according to the disclosed embodiments.

The internal components for the disclosed detection systems may form a low-pass spectral filter system, such as the system 100 illustrated in FIG. 2. The system disclosed by FIG. 2 can be utilized in detection systems 10, 20 and 40 disclosed above. In particular, FIG. 2 illustrates the use of shutters and/or mechanical baffles minimizes extraneous light sources by selectively limiting access of extraneous light (as well as excitation and emission light) to the detector. For example, a shutter within housings 12 and 22, or front part 44 may be triggered to open within a discreet period of time in conjunction with an excitation pulse in order to limit the interference effects of extraneous light sources.

FIG. 2 depicts the components for a low-pass spectral filter detection system 100 according to the disclosed embodiments. System 100 may be incorporated within the hand-held and portable detection systems disclosed above. In particular, the components disclosed by FIG. 2 may be housed within the detection systems disclosed above.

In FIG. 2, excitation energy 102 from one or more excitation (i.e., light) sources 110 within detection system 100 is directed through a spectral filter 140 at a target material 112 in order to generate an emission. Although two light sources 110 are shown, the disclosed embodiments may include any number of excitation sources, including using only a single light source. Preferably, light source or sources 110 may produce narrow-band energy of about 10 nanometers or less. More preferably, the narrow-band energy is about 3 nanometers or less. Light sources 110 may be turned on and off quickly, such as in a range of about or less than 0.01 of a second. Preferably, light sources 110 may be turned on and off within a time period of about 0.001 second.

Emission energy 104 from the targeted material is detected with an optic 114 and is enhanced by a connected low-pass spectral filter 116 prior to being analyzed by a coupled spectrograph/spectrometer 120. Visible light filter 113 may be located in front of optic 114. Visible light filter 113 helps prevent a large spectrum of light from entering the system so that the large spectrum does not overload the subsequent components with information.

Spectrometer 120 is coupled to synchronous detector 121. Synchronous detector 121 is on when light sources 110 are on. Preferably, a return signal of emission energy 104 is received and processed when light sources 110 are on. A problem with optical methods of substance detection is that unwanted light may enter detection system 100. Because of the sensitivity of the components of detection system 100, unwanted light may interfere with the desired light response resulting from light sources 110 (or any illumination source).

Light sources 110 may be modulated within a range of about 100 Hz to 3000 Hz to insure that the response, such as emission energy 104, from target material 112 is the predominate signal received by synchronous detector 121. Synchronous detector 121 is synchronized to this light modulation in phase and frequency. Thus, detection system 100 responds to the desired substance response while rejecting light of other frequencies and phases outside the narrow passband invoked by the filters of detection system 100. Moreover, a detector "on" during the entire process would pick up shakiness or other movements of detection system 100. The disclosed embodiments help mitigate such interference.

Synchronous detector 121 is coupled to integrator 119. The signal detected by synchronous detector 121 is rectified for further processing. Integrator 119 rectifies the AC signal from synchronous detector 121 to a corresponding DC signal or signal with a DC component. The rectification of the signal helps extract the data within the detected signal by subsequent components of detection system 100.

After being rectified by synchronous detector 121 and integrator 119, the resulting data signal is processed and digitized with a digitizer 122. Alternatively, digitizer 122 may receive a voltage signal indicative of the data signal received by spectrometer 120. Signal processor 134 receives and further processes the digitized data, and provides it other components within detection system 100. The collected data may be imaged on a display 124 or reported (e.g., by a buzzer/audible device or a display light) by alert 126.

Detection system 100 also may include a camera 128 for visually recording the target material 112. Detection system 100 also may include various communication devices 132 (e.g., a cell phone, GPS module, a wireless interface) as well as a data storage mechanism. These devices may transmit and receive information from other sources, and be used to backup information detected and generated by detection system 100. Devices 132 also may be modular in that they are separable from detection system 100 as needed.

Detection system 100 also may include a distance sensor 130 for measuring the offset distance of the device from the targeted material. Red passband filter 131 is located between distance sensor 130 and target material 112. Distance sensor 130 may provide different results due to different surfaces within target material 112. Red passband filter 131 filters light received to narrow the spectral bandwidth, and to reduce these differences. Red passband filter 131 also may be known as an optical distance filter.

Distance sensor 130 provides distance to target information for detection system 100. Thus, detection system 100 may keep the detection threshold approximately constant over a period of time by accurately setting the system gain in real-time. Errors in distance determination, therefore, may result in fluctuations in the detection threshold and possible false alarms or non-detects. Red passband filter 131 helps prevent such errors. Moreover, an output of distance sensor 130 is used to adjust an indicator for $1/R^2$ energy falloff, where R is the determined target-to-system distance. The indicator may be used to alert a user that the distance between detection system 100 and target material 112 may result in an erroneous reading.

To provide better distance determination results, an angle 152 between a central ray 150 from light source 110 and an optical axis is adjustable to reduce energy from non-Lambertian surface reflections from unwanted substances or surfaces. Not every surface of target material 112 is smooth and reflective, and this feature allows detection system to account for such reflections that may distort analysis by subsequent components.

Thus, the output of synchronized detector 121 may be rectified, processed and filtered to produce a resultant DC voltage that constitutes the response from target material 112. This signal from synchronized detector 121 is digitized or compared to a fixed voltage to provide an indication of detection or non-detection of a substance of interest.

Regardless of the particular configuration, the sensitivity limits of the system can depend on any of several factors. These factors can include: energy source availability, cross-section of photoelectric absorption, path length, detector collecting area, detector spectral resolution, detector geometrical characteristics, integration time, and detector noise limit. A number of steps have been taken to maximize these factors for detection.

The disclosed system may use a continuous output deuterium ultraviolet source with narrow-band interference filter(s) to define the excitation spectral properties. In such an arrangement, the power density available at full output power is $1$ mW/cm$^2$. The UV to VIS output is collected by a 3 cm$^2$ area lens and directed from the target area to the detection system. The lens collects energy from a concentrated illuminated spot (about 100 mm diameter) on a target at an approximately 300 mm standoff.

The cross-section of the target is optimized for photoelectric absorption by selecting a fixed spectral filter or by using a monochromator to provide the required excitation wavelength for each substance of interest in the target area. Simultaneously, a receiver comprising a spectrograph and light-sensitive detector views the target area. Thereafter, quick emission samples (or exposures) are recorded and the resultant spectra compared to a database of known substances. Using this system, detection sensitivities of approximately 100 nanograms/cm$^2$ with methamphetamine have been achieved in a 2 inch diameter area at a standoff distance of 12 inches.

The disclosed system also provides the ability to detect and analyze substances within target areas at substantial standoff distances whether in liquid, solid or gaseous form. The disclosed system also may be adapted to be use in unique and varied system configurations (including critical component placement). The disclosed system includes the creation, update and maintenance of a database of unique signatures for individual and complex mixtures of substances. In this regard, the invention can utilize miniature spectrograph instruments coupled to detector arrays with high efficiency power capabilities and novel source optics design.

The disclosed systems include hand held devices for the detection of unknown substance, including, for example, methamphetamine and its chemical precursors. These embodiments of the invention enable real time detection of illicit drugs and illicit drug production. Detection of methamphetamine, for example, is accomplished by passing the spectral beam over a surface contaminated with trace quantities of methamphetamine. In this regard, the invention is well suited for addressing issues related to the illicit production and distribution of amphetamine and amphetamine-like substances.

For example, illegal laboratories that manufacture methamphetamines are one of the greatest challenges facing law enforcement officers. Remediation of methamphetamine laboratories is a required step prior to permitting re-occupancy of the house or other contaminated structure where an illicit lab was located because residual chemicals may pose health concerns in residential structures even after the laboratory equipment has been removed.

Figure 3:
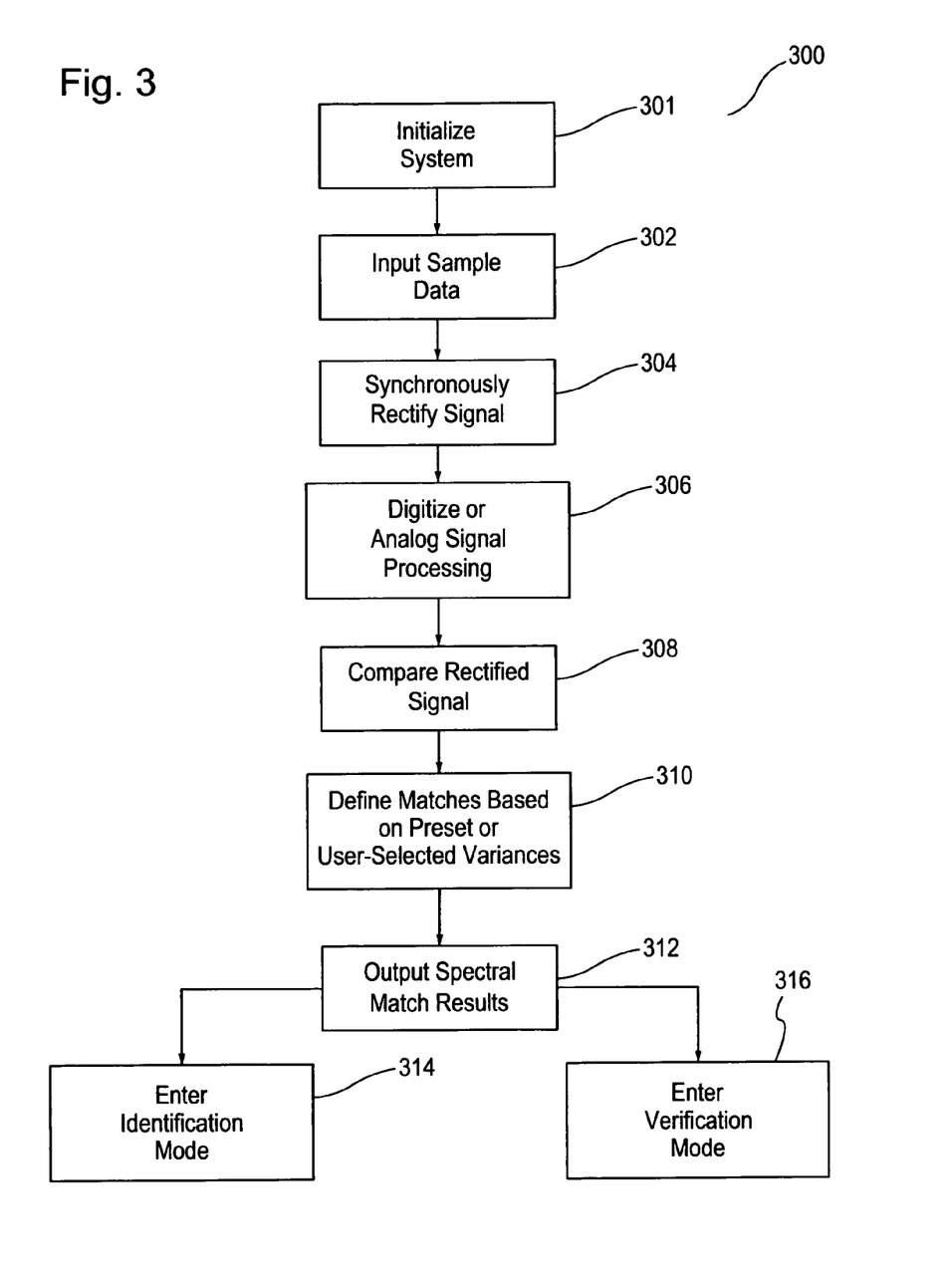
FIG. 3 illustrates a flowchart for matching measured photoemission data with known signature spectra of certain compounds according to the disclosed embodiments.

FIG. 3 depicts a flowchart 300 for matching measured photoemission data with known signature spectra of certain compounds according to the disclosed embodiments. In FIG. 3, step 301 executes by initializing the detection system, such as detection system 100. Step 302 executes by inputting sample data. The data from an evolving sample spectrum being acquired is supplied to the system. Step 304 executes by synchronously rectifying the signal received by detection system 100. The signals received by synchronous detector 121 are rectified.

Step 306 executes by digitizing or performing analog signal processing. Detection system 100 may apply algorithms to the acquired sample data. This step can include, for example, application of a 20th order power series of cosine functions for curve matching or an FFT analysis.

Step 308 executes by comparing the rectified or digitized signal to the UV signatures loaded from a database. Step 308 can include, for example, using a least-square curve-fitting routine or FFT that reduces the measured spectrum to a small set of digital numbers sufficient to describe the key information contained in the spectrum, including using up to a 24th-order equation to manipulate the digitized information (or its coefficients if transformed to frequency space by an FFT).

Step 310 executes by defining matches based on preset or user-selected variances. Detection system 100 determines whether there has been a match based on the comparison procedure in step 308. A match can be defined as a preset standard deviation between values from the sample spectrum and those of stored spectra, such as, for example, three standard deviations above or below an average value of a stored spectrum).

Step 312 executes by outputting spectral match results. Detection system 100 outputs the results of any matches. Step 312 can include either (or both) of steps 314 (in which the system provides spectral results for visual inspection by the operator and/or provides overlays of the produced spectra) and step 316 (in which visual and/or audible alarms indicate a match). Step 314 executes by entering an identification mode, as disclosed above. Step 316 executes by entering a verification mode, also disclosed above.

The disclosed embodiments allow for an extensive number of applications. A non-exclusive list includes, but is not limited to: any industries, processes and/or equipment requiring remote, non-invasive sensing of multiple chemical compounds or constituents (such as in the chemical, petroleum and other similar industries, internal pollution and contamination controls, external pollution and contamination controls, illegal drug detection and monitoring, commercial drug quality control and dispensing verification, nuclear waste and effluent monitoring, air standards determination, explosives monitoring and detection, semiconductor industry effluent monitoring and control, hazardous waste and emission monitoring, semiconductor quality control measures, semiconductor processing contamination monitoring and control, plasma monitoring and control, waste dump site monitoring and control, nuclear, biological, and chemical weapons by-products monitoring, clean room monitoring and control, clean room tools monitoring, vacuum controls, laminar flow controls and controlled environments); security monitoring (including airport and transportation security, improvised explosive device (IED) detection, military and civilian ship and building security, drug (illegal and commercial) security, explosives, weapons and bio-hazard manufacture, detection and storage); remediation (including of hazardous and toxic materials, chemicals, buried land mines, unexploded ordinance, and other explosive devices).

It will be apparent to those skilled in the art that various modifications and variations can be made in the disclosed embodiments of the privacy card cover without departing from the spirit or scope of the invention. Thus, it is intended that the present invention covers the modifications and variations of the embodiments disclosed above provided that the modifications and variations come within the scope of any claims and their equivalents.

What is claimed is:

1. A handheld photoemission spectroscopy detection system comprising:
 a miniature scanning detection system operating in the ultraviolet portion of the electromagnetic spectrum comprising:
 an excitation light source, wherein an angle between a central ray from the excitation light source and an optical axis is adjustable;
 a low-pass spectral filter;
 a visible light filter;
 an ultraviolet fluorescence detector to detect a plurality of emissions;
 a synchronous detector synchronized to a phase or a frequency of the excitation light source to detect a signal of interest from the plurality of emissions;
 a processor coupled to the synchronous detector, the processor receiving spectral data from the signal of interest; and
 a database coupled to said processor that includes signature data for a plurality of predetermined chemical substances to compare to the spectral data.

2. The system of claim 1, wherein said excitation light source produces a narrow-band of three nanometers or less, and comprises at least one of a light emitting diode, a laser, a laser diode, a flashlamp and combinations thereof.

3. The system of claim 1, wherein said excitation light source comprises at least one of a pulsed light source, a square-wave modulated light source, a continuous wave light source and combinations thereof.

4. The system of claim 1, wherein said system determines a distance to a target with an optical distance sensor.

5. The system of claim 4, wherein an output of the optical distance sensor is used to adjust an indicator for $1/R^2$ energy falloff, where R is the determined target-to-system distance.

6. The system of claim 5, further comprising a red passband filter used in conjunction with the optical distance sensor.

7. The system of claim 1, further comprising an integrator to rectify the signal of interest from the synchronous detector.

8. The system of claim 1, further comprising a global positioning system (GPS).

9. The system of claim 1, wherein said system has a functional standoff distance of approximately 2 inches to approximately 12 inches.

10. The system of claim 1, further comprising at least one of optics, a spectrograph and a detector array.

11. The system of claim 1, wherein said system operates with a radiation wavelength range of approximately 200 nanometers to approximately 700 nanometers.

12. The system of claim 1, wherein the angle between a central ray from the excitation light source and an optical axis is adjustable to reduce energy from non-Lambertian surface reflections from unwanted substances or surfaces.

13. A method for detecting a substance using a handheld photoemission spectroscopy detection system, the method comprising:
 operating a miniature scanning detection system in the ultraviolet portion of the electromagnetic spectrum, wherein the miniature scanning detection system includes an ultraviolet fluorescence detector to operate in conjunction with
  an excitation light source, wherein an angle between a central ray from the excitation light source and an optical axis is adjustable,
  a low-pass spectral filter,
  a synchronous detector, and
  a visible light filter;
 receiving composite spectral data from the ultraviolet fluorescence detector at the synchronous detector, wherein the synchronous detector detects a signal of interest from the composite spectral data;
 retrieving signature data for a predetermined chemical substance from a database coupled to the processor based on the signal of interest; and
 outputting matched signature data.

14. A handheld photoemission spectroscopy detection system comprising:
 a miniature scanning detection system operating in the ultraviolet portion of the electromagnetic spectrum including
  a plurality of light emitting diodes (LEDs), wherein each of the plurality of LEDs emit within a specified portion of the spectrum, and further wherein an angle between a central ray of the plurality of LEDs and an optical axis is adjustable;
  at least one low-pass spectral filter;
  a visible light filter;
  a spectrometer to detect a plurality of emissions from the plurality of LEDs;
  a synchronous detector coupled to the spectrometer, and synchronized to a phase or a frequency of the plurality of LEDs to detect a signal of interest from the plurality of emission;
 a processor coupled to the spectrometer to receive spectral data corresponding to the signal of interest; and
 a database coupled to said processor that includes signature data for a plurality of predetermined chemical substances, wherein the database provides signature data that matches the spectral data of the signal of interest to identify at least one of the plurality of predetermined chemical substances.

15. The system of claim 14, further comprising a red passband filter.

* * * * *